United States Patent [19]

Homeier et al.

[11] 4,329,521
[45] May 11, 1982

[54] OXO ALCOHOL SYNTHESIS WITH RHODIUM CATALYST RECYCLE

[75] Inventors: Edwin H. Homeier, Maywood; Tamotsu Imai, Mt. Prospect; David E. Mackowiak, Des Plaines; Catherine E. Guzolek, Park Ridge, all of Ill.

[73] Assignee: UOP Inc., Des Plains, Ill.

[21] Appl. No.: 239,960

[22] Filed: Mar. 3, 1981

Related U.S. Application Data

[63] Continuation of Ser. No. 138,819, Apr. 9, 1980, abandoned.

[51] Int. Cl.³ .............................................. C07C 27/22
[52] U.S. Cl. ...................................... 568/909; 252/412
[58] Field of Search ......................................... 568/909

[56] References Cited

U.S. PATENT DOCUMENTS

| | | | |
|---|---|---|---|
| 3,369,050 | 2/1968 | Green | 568/909 |
| 3,501,531 | 3/1970 | Wilkinson | 568/909 |
| 3,594,425 | 7/1971 | Brader et al. | 568/909 |
| 3,857,895 | 12/1974 | Booth | 568/909 |
| 3,896,047 | 7/1975 | Aycock et al. | 568/909 |
| 3,904,547 | 9/1975 | Aycock et al. | 568/909 |
| 3,954,877 | 5/1976 | Gipson | 568/909 |
| 4,061,687 | 12/1977 | Kaufhold et al. | 568/909 |
| 4,292,196 | 9/1981 | Homeier et al. | 568/909 |

*Primary Examiner*—Joseph E. Evans
*Attorney, Agent, or Firm*—James R. Hoatson, Jr.; Raymond H. Nelson; William H. Page, II

[57] ABSTRACT

Alcohols may be synthesized by treating an olefinic hydrocarbon with carbon monoxide and hydrogen in a hydroformylation zone using a rhodium complex catalyst and an amine modifier to effect the reaction. Following the formation of the alcohol, a catalyst may be extracted from said alcohol by treatment with an aqueous ammonium hydroxide solution. Following this, the aqueous ammonium solution containing the rhodium catalyst is subjected to an extraction process utilizing the amine modifier as the extractant and thereafter recycling the rhodium complex catalyst and amine modifier to the hydroformylation zone.

16 Claims, 1 Drawing Figure

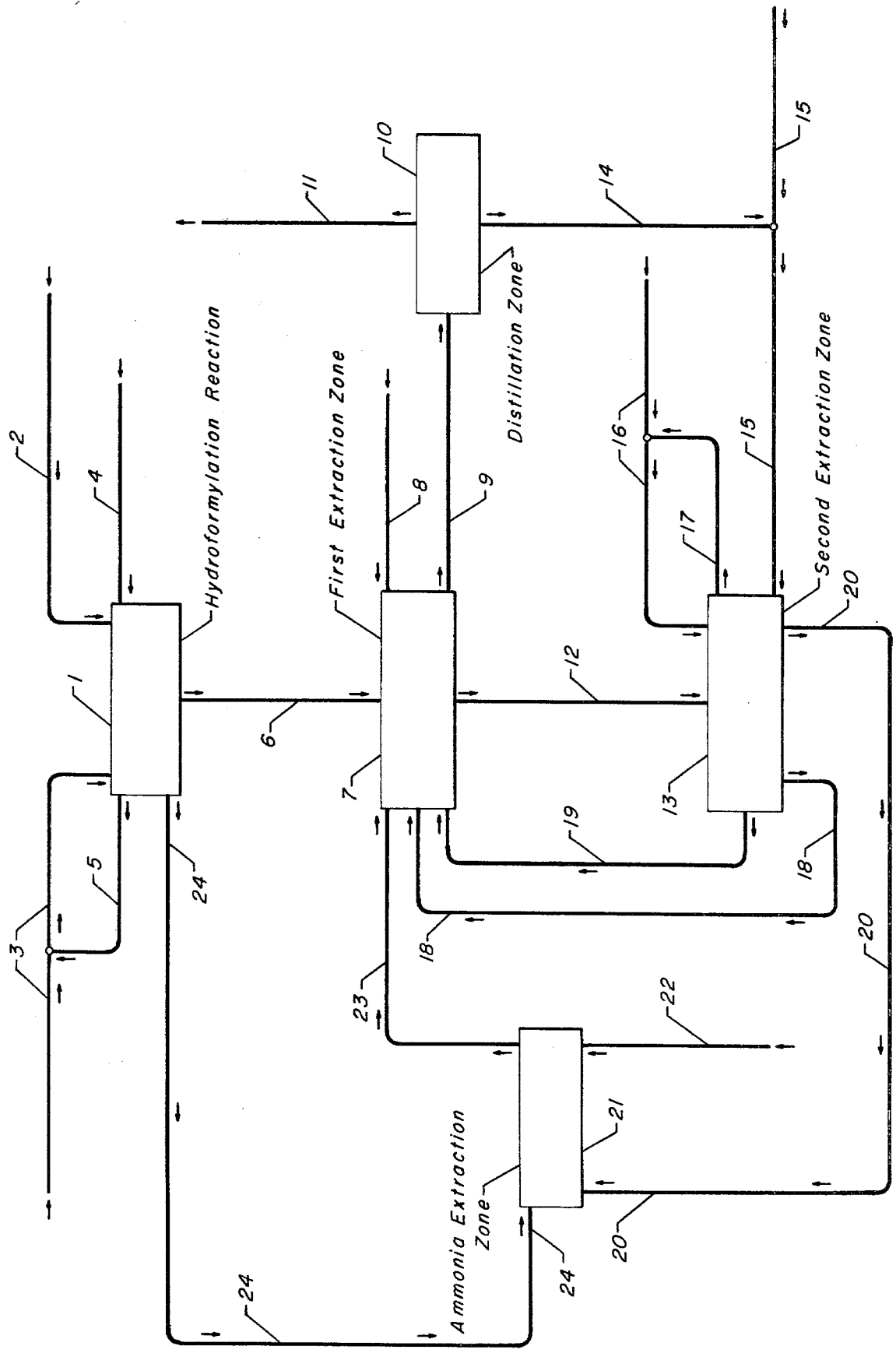

OXO ALCOHOL SYNTHESIS WITH RHODIUM CATALYST RECYCLE

RELATED APPLICATIONS

This application is a continuation of our copending application, Ser. No. 138,819 filed Apr. 9, 1980 now abandoned.

This invention relates to a process for the synthesis of alcohols. More specifically, the invention is concerned with a process for synthesizing alcohols by treating an olefinic hydrocarbon with carbon monoxide and hydrogen in the presence of a rhodium complex catalyst, said catalyst then being recovered in a series of steps hereinafter set forth in greater detail and recycled for further use.

Alcohols are important basic chemicals which find a wide variety of uses in industry. For example, ethyl alcohol is a basic chemical which is used as a solvent and in the manufacture of intermediates, dyes, synthetic drugs, synthetic rubbers, detergents, cleaning source, surface coatings, cosmetics, pharmaceuticals, rocket fuel, beverages, etc. Isopropyl alcohol is used in the manufacture of acetone which in turn is a source of acetic anhydride, diacetone alcohol, methyl isobutyl ketone and other derivatives is also used as a solvent for essential oils, gums, resins; as a latent solvent for cellulose derivatives; as an anti-stalling agent in liquid fuels or as an intermediate in the manufacture of pharmaceuticals, perfumes, lacquers, rocket fuel, etc. Likewise, dodecyl alcohol which is also known as lauryl alcohol is used in the manufacture of synthetic detergents, lube additives, pharmaceuticals, rubber, textiles, and perfumes. Tetradecanol which is also known as myristyl alcohol is used in organic synthesis, as a plasticizer, antifoam agent, as a perfume fixitive for soaps and cosmetics as well as other uses.

The prior art has shown, as exemplified by the Oxo process, that aldehydes may be produced from olefinic hydrocarbons by treatment with carbon monoxide and hydrogen using a cobalt carbonyl catalyst. It has further been shown in the prior art, as exemplified by U.S. Pat. No. 2,880,241, that rhodium is known to be a much more active catalyst than cobalt. The activity and selectivity of rhodium catalysts may be altered by modifying the catalyst with other compounds such as tertiary amines. For example, when using tertiary amines to modify rhodium catalysts, it is possible to produce alcohols rather than aldehydes in this process.

The commercialization of processes for the synthesis of alcohols utilizing rhodium complex catalysts is affected by the difficulty which is attendant in the recovery of rhodium, a particular disadvantage which negates the commercial use of such catalyst complexes comprising the frequent losses of the precious metal which may occur under process conditions, the loss of only a trace amount of this precious metal making the process uneconomical to operate and overshadowing the technological attractive conversion rate and selectivity rate which is obtained when using this metal. The separation of the rhodium catalyst from alcohol products, especially high molecular weight alcohols by conventional means such as distillation, is not practical inasmuch as the unstable rhodium-amine complex decomposes in a distillation apparatus, thus resulting in the loss of the rhodium by plating or precipitation on the surfaces of the processing equipment.

Inasmuch as a particular advantage of utilizing a one-step synthesis of alcohol lies not only in a lower process cost and capital cost, when compared with the conventional Oxo process to produce aldehydes, but also results in a higher yield of the desired products. This is particularly advantageous inasmuch as a loss of aldehydes which easily takes place during distillation via their condensation in a still does not occur in this process.

It is therefore an object of this invention to provide a process for the synthesis of alcohol utilizing a recovery system for the catalyst. A further object of this invention is found in a one step process for the synthesis of alcohols utilizing a precious metal catalyst such as a rhodium complex catalyst which is easily recoverable and reusable in the process.

In one aspect an embodiment of this invention resides in a process for the synthesis of an alcohol which comprises the steps of treating an olefinic hydrocarbon with carbon monoxide and hydrogen in a hydroformylation zone at hydroformylation reaction conditions in the presence of a rhodium complex catalyst and an amine modifier; extracting said rhodium complex catalyst from the resulting alcohol by treatment with an aqueous ammonium hydroxide solution at treating conditions; separating the product alcohol and amine modifier from said aqueous ammonium hydroxide solution containing said catalyst; separating and recovering said alcohol from said modifier; extracting said rhodium complex catalyst from said aqueous ammonium hydroxide solution at extraction conditions in the presence of carbon monoxide using said amine modifier as the extractant; and recycling the rhodium complex catalyst and amine modifier to said hydroformylation zone.

A specific embodiment of this invention is found in a process for the synthesis of an alcohol which comprises treating hendecene with carbon monoxide and hydrogen in a hydroformylation zone at a temperature in the range of from about 50° to about 250° C. and a pressure in the range of from about 5 to about 300 atmospheres in the presence of a catalyst comprising chlorodicarbonylrhodium dimer and a modifier comprising dimethyldodecylamine, extracting said catalyst from the resulting dodecanol by treatment with an aqueous ammonium hydroxide solution at a temperature in the range of from about 20° to about 100° C. and a pressure in the range of from about atmospheric to about 50 atmospheres, separating dodecanol from the dimethyldodecylamine modifier, extracting said catalyst from said aqueous ammonium hydroxide solution at a temperature in the range of from about 20° to about 200° C. and a pressure in the range of from about atmospheric to about 300 atmospheres in the presence of carbon monoxide using said dimethyldodecylamine as the extractant, and recycling said rhodium complex catalyst and said dimethyldodecylamine to said hydroformylation zone.

Other objects and embodiments will be found in the following further detailed description of the present invention.

As hereinbefore set forth the present invention is concerned with a process for the synthesis of alcohols utilizing a rhodium complex catalyst which may be recovered and recycled for further use. The synthesis of the alcohols is effected by reacting an olefinic hydrocarbon with carbon monoxide and hydrogen in the presence of these rhodium complex catalysts and a promoter or modifier comprising a tertiary amine. The reaction conditions which are employed to synthesize the alcohol will include a temperature of from about 50° to about 250° C. and a pressure in the range of from about 50 to about 300 atmospheres. In the preferred embodiment of the invention the pressures which are employed to effect the desired result will be the autogenous pressures resulting from the presence of hydrogen and carbon monoxide in the reaction mixture. However, it is also contemplated within the scope of this invention that the pressures resulting from the use of hydrogen and carbon monoxide will comprise only a partial operating pressure, the remainder being provided for by the introduction of a substantially inert gas such as nitrogen, helium, argon, etc., into the reaction vessel. In addition, other reaction conditions which are present during the synthesis of the alcohol will include a mole ratio of hydrogen to carbon monoxide in the range of from about 0.5:1 to about 5:1 moles of hydrogen per mole of carbon monoxide, a mole ratio of olefin to catalyst in the range of from about 500:1 to about 2000:1 moles of olefin per mole of catalyst and a mole ratio of tertiary amine modifier to catalyst in the range of from about 50:1 to about 300:1 moles of amine per mole of catalyst.

Examples of olefinic hydrocarbons which may be employed to effect the process of this invention will include straight chain olefins containing from 3 to about 30 carbon atoms such as propylene, butene-1, butene-2, pentene-1, pentene-2, hexene-1, hexene-2, hexene-3, heptene-1, heptene-2, heptene-3, octene-1, octene-2, octene-3, octene-4, nonene-1, nonene-2, nonene-3, nonene-4, as well as the isomeric decenes, undecenes, dodecenes, tridecenes, tetradecenes, pentadecenes, hexadecenes, heptadecenes, octadecenes, nonadecenes, eicosenes, henicosenes, docosenes, tricosenes, tetracosenes, pentacosenes, hexacosenes, heptacosenes, octacosenes, nonacosenes, triacontenes, etc.

The reaction between the olefinic hydrocarbon of the type hereinbefore set forth, carbon monoxide and hydrogen is effected in the presence of a rhodium complex catalyst which may be organometallic in nature or which may comprise a salt which is converted to the complex catalyst during the process under the reaction conditions employed. Specific examples of these rhodium catalysts will include rhodium nitrate, rhodium chloride, rhodium bromide, rhodium iodide, rhodium fluoride, chlorodicarbonylrhodium dimer, chlorobis(ethylene)rhodium dimer, hexarhodiumhexadecylcarbonyl, tetrarhodiumdodecylcarbonyl, rhodium acetate, rhodium acetylacetonate, rhodium oxide, etc. Alternatively, rhodium metal may be used, although not necessarily with equivalent results. The modifier which is utilized to selectively form alcohols will comprise a tertiary amine, said tertiary amine including alkyl amines, aryl amines, heterocyclic amines, cycloalkyl amines, etc., such as trimethylamine, triethylamine, tripropylamine, the isomeric tributylamines, tripentylamines, trihexylamines, triheptylamines, trioctylamines, trinonylamines, tridecylamines, dimethylethylamine, dimethylpropylamine, dimethylbutylamine, dimethyldodecylamine, triphenylamine, tribenzylamine, tri-o-tolylamine, tri-m-tolylamine, tri-p-tolylamine, tricyclopentylamine, tricyclohexylamine, N-methylpyridine, N-methylpyran, N-ethylpyridine, N-ethylpyran, etc. It is to be understood that the aforementioned olefinic hydrocarbons, rhodium catalysts and tertiary amines are only representative of the class of compounds which may be employed and that the present invention is not necessarily limited thereto.

After synthesizing the alcohol utilizing the desired reactants, catalysts and operating conditions, the product is recovered and the rhodium complex catalyst is separated therefrom and recovered by extracting the rhodium complex catalyst from the alcohol by treating the alcohol with an aqueous ammonium hydroxide solution. This step of the process is effected at treating conditions which will include a temperature in the range of from about ambient (20°-25° C.) to about 100° C. and a pressure in the range of from about atmospheric to about 50 atmospheres. In the event that superatmospheric pressures are employed in the treating step, the pressures are afforded by the introduction of a substantially inert gas such as nitrogen into the reaction vessel. After allowing the treatment to take place during a period of time which may range from about 0.5 up to about 20 hours or more, the alcohol and amine modifier are separated from the aqueous ammonium hydroxide solution containing the rhodium complex catalyst. This separation may be effected in any suitable manner known in the art such as distillation, decantation, etc. The organic portion is then subjected to a distillation step in which the product alcohol is separated from the amine modifier and recovered. Thereafter the amine modifier is used as an extractant in treating the aqueous ammonium hydroxide solution containing the rhodium complex catalyst. The extraction of the rhodium complex with the amine modifier is also effected at extraction conditions which will include a temperature in the range of from about ambient to about 200° C. and a pressure in the range of from about atmospheric to about 300 atmospheres, the superatmospheric pressures being afforded by the use of a carbon monoxide containing gas such as carbon monoxide or carbon monoxide mixed with other gases such as hydrogen, nitrogen, argon, helium, etc. The rhodium complex catalyst, by this step of the process, will be extracted into the organic phase comprising the amine modifier, said organic phase then being treated to remove any traces of residual ammonia which may be present and thereafter recycled to the hydroformylation zone to be used as a portion of the catalyst amount which is necessary to effect the hydroformylation reaction of an olefinic hydrocarbon of the type hereinbefore set forth in greater detail with carbon monoxide and hydrogen in the hydroformylation reaction zone.

The process of this invention may be effected in any suitable manner and may comprise either a batch or continuous type operation. For example, when a batch type operation is used, a quantity of the olefin which is to be hydroformylated is charged to a pressure resistant apparatus such as an autoclave of the rotating, mixing or stirring type, said apparatus containing the rhodium complex catalyst and the tertiary amine which acts as a modifier. The autoclave is sealed and carbon monoxide and hydrogen pressured in until the desired operating pressure has been attained. Thereafter the reactor is heated to the desired operating temperature and maintained thereat for a predetermined period of time which may range from about 0.5 up to about 10 hours or more in duration. Following the completion of the desired reaction period, heating is discontinued and after the apparatus has returned to room temperature the excess pressure is discharged and the reaction mixture is recovered therefrom. The reaction mixture is then charged to a second apparatus which may also be of the pressure resistant type, if so desired, and the reaction mixture is contacted with an aqueous ammonium hydroxide solution at reaction conditions hereinbefore set forth in greater detail. Upon completion of the extraction or treatment period the aqueous ammonium hydroxide solution containing the extracted rhodium complex catalyst is separated from the organic phase which comprises the product alcohol and the amine modifier. The organic phase may then be subjected to fractional distillation to separate the product alcohol from the amine modifier, the former being passed to storage while the latter is then placed in a third apparatus wherein the aqueous ammonium hydroxide solution containing the rhodium complex catalyst is treated with the amine modifier in an extraction step whereby the rhodium complex catalyst is extracted back into the organic phase, this phase then being utilized to form a portion of the catalyst and modifier in the hydroformylation reaction.

It is also contemplated within the scope of this invention that the process of the present invention may be effected in a continuous manner of operation. When such a type of operation is employed the starting material comprising olefinic hydrocarbon is continuously charged to a reaction zone which is maintained at the proper operating conditions of temperature and pressure and which contains a rhodium complex catalyst as well as a tertiary amine modifier. The desired operating pressures are attained by utilizing the autogenous pressures afforded by the carbon monoxide and hydrogen which are required for the hydroformylation reaction. After passage through the reaction zone for a predetermined period of time the reactor effluent is continuously withdrawn and passed to an extraction zone wherein said effluent is contacted or treated with an aqueous ammonium hydroxide solution also continuously charged to said zone. After passage through the extraction zone the aqueous layer comprising the ammonium hydroxide solution containing the rhodium complex catalyst is separated from the organic phase which comprises the product alcohol and the tertiary amine modifier. The organic phase is then continuously charged to a distillation zone wherein the tertiary amine modifier is separated from the product alcohol which is passed to storage. The tertiary amine modifier is then continuously charged to an extraction zone along with the aqueous phase containing the rhodium complex catalyst. In this second extraction zone the aqueous phase is contacted with the amine modifier under a carbon monoxide pressure, the rhodium complex catalyst being extracted from the aqueous phase and passed into the organic phase, said organic phase being recycled to the hydroformylation zone wherein the rhodium complex catalyst and amine modifier afford a portion of the desired amount of catalyst required for the hydroformylation reaction. It is to be noted that the extraction of the rhodium complex catalyst from the aqueous ammonium hydroxide phase to the organic phase in the second extraction zone is also effected under a carbon monoxide pressure which may range from about atmospheric to about 300 atmospheres, thereby assuring a more complete extraction of the catalyst from the aqueous phase to the organic phase.

BRIEF DESCRIPTION OF THE DRAWING

The present invention will be further illustrated with reference to the accompanying drawing which sets forth a flow diagram of one embodiment of the process of this invention. It is to be understood that various valves, pumps, etc., have been eliminated as not being essential to the complete understanding of the invention. However, the utilization of these as well as other similar appurtenances will become obvious as the drawing is described.

Referring now to the drawing an olefinic hydrocarbon which is to be hydroformylated according to the process of this invention is charged to hydroformylation reaction zone 1 through line 2 along with a rhodium complex catalyst of the type hereinbefore set forth. In addition, a mixture of carbon monoxide and hydrogen is also charged to reaction zone 1 through line 3. In zone 1 the olefinic hydrocarbon is subjected to a hydroformylation reaction at conditions hereinbefore set forth in the presence of a rhodium complex catalyst which has also been charged to reaction zone 1 through line 4. After passage through the reaction zone for a predetermined period of time during which time any carbon monoxide and hydrogen which have not been used up in the reaction are recycled back to zone 1 through lines 5 and 3, the reaction mixture is withdrawn from zone 1 through line 6 and passed to a first extraction zone 7. In extraction zone 7 the organic phase is contacted with an aqueous ammonium hydroxide solution which is charged to zone 7 through line 8. In extraction zone 7 any rhodium complex catalyst which has become entrained or dissolved in the organic phase is separated and extracted therefrom. The organic phase which contains the product alcohol and the tertiary amine modifier are separated from the aqueous phase by means not shown in the drawing and withdrawn from zone 7 through line 9 and passed to distillation zone 10. In distillation zone 10 the amine modifier is separated from the product alcohol, said alcohol being withdrawn through line 11 and passed to storage. The aqueous ammonium hydroxide solution containing the rhodium complex catalyst is withdrawn from extraction zone 7 through line 12 and passed to a second extraction zone 13. In extraction zone 13 the aqueous ammonium hydroxide is contacted with the amine modifier which has been withdrawn from distillation zone 10 through line 14 and charged to extraction zone 13 through lines 14 and 15, any additional makeup amine modifier also being charged to extraction zone 13 through line 15. In addition, carbon monoxide is also charged to extraction zone 13 through line 16 while any unreacted carbon monoxide is recycled through lines 17 and 16 to extraction zone 13.

In extraction zone 13 the aqueous ammonium hydroxide solution containing the rhodium complex catalyst is extractively distilled under the carbon monoxide pressure utilizing the amine modifier as the extractant. The aqueous layer comprising the ammonium hydroxide solution is then recycled to first extraction zone 7 through line 18 while in addition any trace of rhodium which remains in the aqueous phase is also recycled to extraction zone 7 through line 18. The water and ammonia distilled from the aqueous phase in the second extraction zone is also recycled to the first extraction zone through line 19. The organic phase comprising the amine modifier which contains the rhodium complex catalyst along with a trace amount of ammonia is withdrawn from second extraction zone 13 through line 20 and passed to ammonia extraction zone 21 wherein the trace ammonia is removed by a water wash, said water being charged to ammonia extraction zone 21 through line 22. The aqueous phase containing the trace amount of ammonia is withdrawn from extraction zone 21 through line 23 and recycled to the first extraction zone 7. The organic phase comprising the amine modifier containing the rhodium complex catalyst is withdrawn through line 24 and recycled back to hydroformylation reaction zone 1 wherein it is used as a portion of the catalyst and modifier in the hydroformylation of the olefinic hydrocarbon to form the desired alcohol.

The following examples are given to illustrate the process of the present invention. However, it is to be understood that these examples are given merely for purposes of illustration and that the present invention is not necessarily limited thereto.

EXAMPLE I

In this example an olefin charge of 496.11 grams of a $C_{11}$ olefin blend comprising 97% by weight of olefins and 2% by weight of an n-eicosane internal standard along with 149.49 grams of dimethyldodecylamine and 0.9006 grams of chlorodicarbonylrhodium dimer were charged to a 3 liter pyrex lined rotating autoclave. The autoclave was sealed and 150 atmospheres of a 1:1 blend of carbon monoxide and hydrogen was charged thereto at room temperature. The autoclave was then heated to a temperature of 150° C. and maintained thereat for a period of 6 hours. At the end of this time the autoclave was allowed to return to room temperature, the excess pressure was discharged and the reaction mixture was recovered therefrom. The deep red hydroformylation product was analyzed by standard gas liquid chromatographic analysis to determine that there had been a 100% conversion of the olefins with a 99.8% mole selectivity to dodecyl alcohols.

EXAMPLE II

A portion of the product prepared according to Example I above (367.42 grams) along with 356.6 grams of an aqueous ammonium hydroxide solution containing 29% by weight of ammonia were stirred in a glass flask for a period of 16 hours under a nitrogen atmosphere. The dark green aqueous phase was separated in a separatory funnel under a nitrogen blanket and analyzed for rhodium by atomic absorption. Analysis of the aqueous phase determined that it contained 604 ppm of rhodium, comprising 95.3% of the rhodium charged.

EXAMPLE III

To illustrate the extraction of rhodium from the aqueous phase 41.50 grams of the ammonium hydroxide solution containing 0.008 grams of rhodium (193 ppm by weight) and 2.63 grams of dimethyldodecylamine were placed in a stirred glass flask under 1 atmosphere of carbon monoxide. The flask was heated to a temperature of from 40° C. for a period of 5 hours. At the end of this period the red-brown organic phase was separated from the aqueous phase in a separatory funnel under a blanket of nitrogen. Analysis of the phases by atomic absorption indicated that the organic phase contained 2522 ppm by weight of rhodium comprising 78.7% of the rhodium while the aqueous phase contained 60 ppm by weight of rhodium, comprising 21.3% of the rhodium.

EXAMPLE IV

When other catalysts such as rhodium acetylacetonate or hexarhodiumhexadecylcarbonyl are used as catalysts in the treatment of other olefins such as hexene, octene, pentene, nonadecene, with carbon monoxide and hydrogen and utilizing other amine modifiers such as triheptylamine or dimethylphenylamine to form heptanol, nonanol, hexanol and eicosanol, it may be possible to recover the rhodium containing catalysts in a manner similar to that set forth in the above examples.

We claim as our invention:

1. A process for the synthesis of an alcohol which comprises the steps of:
   (a) treating an olefinic hydrocarbon having at least 3 carbon atoms with carbon monoxide and hydrogen in a hydroformylation zone at hydroformylation reaction conditions in the presence of a rhodium complex catalyst and an amine modifier to form an alcohol;
   (b) extracting said rhodium complex catalyst from the resulting alcohol by extraction with an aqueous ammonium hydroxide solution at extraction conditions to obtain an organic phase containing the alcohol and amine and an aqueous ammonium hydroxide solution phase containing the rhodium complex catalyst;
   (c) separating the product alcohol and amine modifier from said aqueous ammonium hydroxide solution containing said catalyst;
   (d) separating and recovering said alcohol from said amine modifier;
   (e) extracting said rhodium complex catalyst from said aqueous ammonium hydroxide solution at extraction conditions in the presence of carbon monoxide using said amine modifier as the extractant; and
   (f) recycling the rhodium complex catalyst and amine modifier to said hydroformylation zone.

2. The process as set forth in claim 1 in which said hydroformylation reaction conditions include a temperature in the range of from about 50° to about 250° C. and a pressure in the range of from about 50 to about 300 atmospheres.

3. The process as set forth in claim 1 in which said rhodium extraction conditions with an aqueous ammonium hydroxide solution include a temperature in the range of from about 20° to about 100° C. and a pressure in the range of from about atmospheric to about 50 atmospheres.

4. The process as set forth in claim 1 in which said rhodium extraction conditions in the presence of carbon monoxide with said amine modifier include a temperature in the range of from about 20° to about 200° C. and a pressure in the range of from about atmospheric to about 300 atmospheres.

5. The process as set forth in claim 1 in which said olefinic hydrocarbon contains from 3 to about 30 carbon atoms.

6. The process as set forth in claim 1 in which said rhodium complex catalyst comprises chlorodicarbonylrhodium dimer.

7. The process as set forth in claim 1 in which said rhodium complex catalyst comprises rhodium.

8. The process as set forth in claim 1 in which said aqueous ammonium hydroxide solution contains from about 5 to about 30% by weight of ammonia.

9. The process as set forth in claim 1 in which said amine modifier comprises dimethyldodecylamine.

10. The process as set forth in claim 1 in which said amine modifier comprises triheptylamine.

11. The process as set forth in claim 1 in which said amine modifier comprises dimethylphenylamine.

12. The process as set forth in claim 1 in which said olefinic hydrocarbon is hexene and said alcohol is heptanol.

13. The process as set forth in claim 1 in which said olefinic hydrocarbon is octene and said alcohol is nonanol.

14. The process as set forth in claim 1 in which said olefinic hydrocarbon is pentene and said alcohol is hexanol.

15. The process as set forth in claim 1 in which said olefinic hydrocarbon is hendecene and said alcohol is dodecanol.

16. The process as set forth in claim 1 in which said olefinic hydrocarbon is nonadecene and said alcohol is eicosanol.

* * * * *